US011033240B2

(12) United States Patent
Chen et al.

(10) Patent No.: US 11,033,240 B2
(45) Date of Patent: Jun. 15, 2021

(54) METHOD AND APPARATUS FOR DETECTING BODY-RELATED TEMPERATURE CHANGES

(71) Applicant: Nokia Technologies Oy, Espoo (FI)

(72) Inventors: Yue Chen, Beijing (CN); Yuyang Liang, Beijing (CN); Peng Lan, Beijing (CN); Wenya Zhao, Beijing (CN); Dandan Wang, Beijing (CN)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/560,748

(22) PCT Filed: Mar. 27, 2015

(86) PCT No.: PCT/CN2015/075233
§ 371 (c)(1),
(2) Date: Sep. 22, 2017

(87) PCT Pub. No.: WO2016/154805
PCT Pub. Date: Oct. 6, 2016

(65) Prior Publication Data
US 2018/0085070 A1    Mar. 29, 2018

(51) Int. Cl.
*A61B 5/00* (2006.01)
*A61B 5/01* (2006.01)

(52) U.S. Cl.
CPC ............ *A61B 5/746* (2013.01); *A61B 5/0008* (2013.01); *A61B 5/01* (2013.01); *A61B 2503/06* (2013.01);
(Continued)

(58) Field of Classification Search
CPC ......... A61B 5/746; A61B 5/0008; A61B 5/01; A61B 2562/0271; A61B 2503/06; A61B 2560/0252
See application file for complete search history.

(56) References Cited

U.S. PATENT DOCUMENTS 7,052,472 B1    5/2006  Miller et al. ............... 600/549
7,410,291 B2 *  8/2008  Koch ...................... G01K 1/20
                                                    374/102
(Continued)

FOREIGN PATENT DOCUMENTS

CN    1294372 A      5/2001
CN    201429893 Y    3/2010
(Continued)

OTHER PUBLICATIONS

Extended European Search Report for corresponding European Patent Application No. 15886792.9, dated Sep. 25, 2018, 7 pages.
(Continued)

*Primary Examiner* — Navin Natnithithadha
*Assistant Examiner* — Andrey Shostak
(74) *Attorney, Agent, or Firm* — Harrington & Smith

(57) ABSTRACT

Methods and apparatuses (10) for detecting body-related temperature changes are provided. The method comprises measuring a skin-surface temperature at a first temperature sensor element (12) at a measuring rate (S21) and measuring an ambient temperature at a second temperature sensor element (13) at the measuring rate (S22). The method also comprises calculating a plurality of first change rates for the skin-surface temperature and a plurality of second change rates for the ambient temperature over a time interval (S23). The method further comprises determining, based on the plurality of first change rates and the plurality of second change rates, whether an ambient temperature change rate is faster than a skin-surface temperature change rate by a threshold (S24). The method additionally comprises selecting whether or not to trigger an alarm based on a result of the determining (S25). With the methods and apparatuses (10), the number of false alarms may be significantly reduced.

10 Claims, 10 Drawing Sheets

(52) U.S. Cl.
CPC ............... *A61B 2560/0252* (2013.01); *A61B 2562/0271* (2013.01)

(56) References Cited

U.S. PATENT DOCUMENTS

| | | | |
|---|---|---|---|
| 8,830,068 B2 | 9/2014 | Campbell et al. | |
| 8,922,365 B2 | 12/2014 | Liu | |
| 2007/0038141 A1* | 2/2007 | Koch | G01K 1/20 600/549 |
| 2012/0068848 A1* | 3/2012 | Campbell | A61B 5/0008 340/573.1 |
| 2012/0112903 A1* | 5/2012 | Kaib | A61N 1/3993 340/539.12 |
| 2014/0129010 A1* | 5/2014 | Garg | G06F 17/00 700/94 |
| 2015/0081136 A1 | 3/2015 | Sutherland et al. | |

FOREIGN PATENT DOCUMENTS

| | | |
|---|---|---|
| CN | 201576343 U | 9/2010 |
| CN | 201638355 U | 11/2010 |
| CN | 201638357 U | 11/2010 |
| CN | 201716826 U | 1/2011 |
| CN | 201757683 U | 3/2011 |
| CN | 102564616 A | 7/2012 |
| CN | 103646495 A | 3/2014 |
| CN | 103968506 A | 8/2014 |
| CN | 204105949 U | 1/2015 |
| EP | 2243422 A1 | 10/2010 |
| GB | 2346560 A | 8/2000 |
| JP | 2008-048819 U | 3/2008 |
| WO | 2014/060938 A1 | 4/2014 |

OTHER PUBLICATIONS

"Now There's a Smart BABYGROW: Parents Can Monitor a Baby's Breathing Rate, Temperature and Sleep Pattern Using Their Smartphone", Mail Online, Retrieved on Sep. 12, 2017, Webpage available at : http://www.dailymail.co.uk/sciencetech/article-2536587/Now-theres-smart-BABYGROW-Parents-monitor-babys-heart-rate-temperature-sleep-pattern-using-smartphone.html.

International Search Report and Written Opinion for corresponding Patent Cooperation Treaty Application No. (PCT/CN2015/075233), dated Dec. 17, 2015, 12 pages.

* cited by examiner

METHOD AND APPARATUS FOR DETECTING BODY-RELATED TEMPERATURE CHANGES

RELATED APPLICATION

This application was originally filed as Patent Cooperation Treaty Application No. PCT/CN2015/075233 filed Mar. 27, 2015.

TECHNICAL FIELD

The example embodiments of the present disclosure generally relate to a temperature monitoring field. More particularly, the example embodiments of the present disclosure relate to methods and apparatuses for detecting body-related temperature changes.

BACKGROUND

For each family, how to prevent children from being sick has become a common concern for the parents since a sick child may not only cost parents' time, energy, and money, but also decrease the child's own immunity. According to the results of many investigations and observations, children get cold and fever mostly because they often kick their quilts or blankets during the nighttime while sleeping. In hope to keep their children far from sickness, many parents have to keep eyes on the children and cover the quilt for them when the quilt is kicked at the nighttime, which may make parents poor sleeping quality and sometimes severely affect their daily life the next day.

In view of the above kicking-quilt situations which may occur to the children or patients, some techniques are developed for alerting the parents or health workers when this kicking-quilt event takes place. These techniques are collectively referred to as "Tipi" alarm techniques. In the existing Tipi alarm techniques, whether the child kicked the quilt or not is determined simply by measuring the temperature of the children's skin through one temperature sensor and comparing the measured temperature with a pre-determined threshold. If the measured temperature is less than the pre-determined threshold, then it may be determined that the child at issue kicked the quilt and is very likely to get cold. However, this Tipi solution works only on the most ideal circumstance as shown in FIG. 1.

The plot as illustrated in FIG. 1 shows a monitoring curve of skin temperature changes occurring at February 5, from 01:06:03 am to 04:04:01 am for a child. As shown, the horizontal axis denotes monitoring times with a time interval of 4 minutes and 14 seconds, and the vertical axis denotes monitored skin temperatures with a 5 degree interval. From the curve, it can be seen that, for the most of the above timeframe, the skin temperature of the child remains relatively stable and, at about 03:03:00 am, the skin temperature sharply drops. Due to this sharp dropping, the existing Tipi alarm technique may simply make a judgment that the kicking-quilt event occurs at the 03:03:00 am and may further warn the parents to cover the quilt for the child.

However, the actual skin temperature during sleeping at nighttime frequently changes, and most importantly, not every temperature changing is caused by Tipi, but due to other situations, for example, dreaming, fever etc., according to real temperature data from the experiment shown in FIG. 2.

As seen from FIG. 2, the monitored skin temperatures dramatically drop nearly five times as indicated by the arrows. According to the existing Tipi technique, there would be five times of warning to the parents accordingly. However, according to the experiment's statistics, some of these temperature-dropping are not due to the kicking-quilt but due to the dreaming. Therefore, the existing Tipi technique may provide some false alarms and if such false alarms are numerous, it may definitely get parents annoyed and exhausted.

SUMMARY

In order to diminish or alleviate at least some of the above problems, some example embodiments of the subject matter defined herein would provide effective and efficient manners for precisely monitoring the skin-surface and ambient temperature changes and providing correct and true alarms for events, such as the Tipi, thereby avoiding the false alarms as much as possible and giving the alarm accuracy a big boost.

According to one aspect of the present disclosure, there is provided a method, which comprises measuring a skin-surface temperature at a first temperature sensor element at a measuring rate. The method also comprises measuring an ambient temperature at a second temperature sensor element at the measuring rate. The method further comprises calculating a plurality of first change rates for the skin-surface temperature and a plurality of second change rates for the ambient temperature over a time interval. The method further comprises determining, based on the plurality of first change rates and the plurality of second change rates, whether an ambient temperature change rate is faster than a skin-surface temperature change rate by a threshold. The method additionally comprises selecting whether or not to trigger an alarm based on a result of the determining.

According to another aspect of the present disclosure, there is provided an apparatus, which comprises a first temperature sensor element for measuring a skin-surface temperature. The apparatus also comprises a second temperature sensor element for measuring an ambient temperature. The apparatus further comprises a communication interface for communicating with at least one external device. The apparatus also comprises at least one processor and at least one memory including computer program code, wherein the at least one memory and the computer program code are configured to, working with the at least one processor, cause the apparatus at least to measure the skin-surface temperature at the first temperature sensor element at a measuring rate. The at least one memory and the computer program code are also configured to, working with the at least one processor, cause the apparatus at least to measure the ambient temperature at the second temperature sensor element at the measuring rate. The at least one memory and the computer program code are also configured to, working with the at least one processor, cause the apparatus at least to calculate a plurality of first change rates for the skin-surface temperature and a plurality of second change rates for the ambient temperature over a time interval. The at least one memory and the computer program code are further configured to, working with the at least one processor, cause the apparatus at least to determine, based on the plurality of first change rates and the plurality of second change rates, whether an ambient temperature change rate is faster than a skin-surface temperature change rate by a threshold. The at least one memory and the computer program code are additionally configured to, working with the at least one processor, cause the apparatus at least to select whether or not to trigger an alarm based on a result of the determining.

According to one aspect of the present disclosure, there is provided a method which comprises receiving temperature data from a thermometer apparatus, wherein the thermometer apparatus comprises a first temperature sensor element for measuring a skin-surface temperature at a measuring rate and a second temperature sensor element for measuring an ambient temperature at the measuring rate. The method also comprises calculating, based on the received temperature data, a plurality of first change rates for the skin-surface temperature and a plurality of second change rates for the ambient temperature over a time interval. The method further comprises determining, based on the plurality of first change rates and the plurality of second change rates, whether an ambient temperature change rate is faster than a skin-surface temperature change rate by a threshold. The method additionally comprises selecting whether or not to trigger an alarm based on a result of the determining.

According to another aspect of the present disclosure, there is provided an apparatus, which comprises at least one processor and at least one memory including computer program code. The at least one memory and the computer program code are configured to, working with the at least one processor, cause the apparatus at least to receive temperature data from a thermometer apparatus, wherein the thermometer apparatus comprises a first temperature sensor element for measuring a skin-surface temperature at a measuring rate and a second temperature sensor element for measuring an ambient temperature at the measuring rate. The at least one memory and the computer program code are also configured to, working with the at least one processor, cause the apparatus at least to calculate, based on the received temperature data, a plurality of first change rates for the skin-surface temperature and a plurality of second change rates for the ambient temperature over a time interval. The at least one memory and the computer program code are further configured to, working with the at least one processor, cause the apparatus at least to determine, based on the plurality of first change rates and the plurality of second change rates, whether an ambient temperature change rate is faster than a skin-surface temperature change rate by a threshold. The at least one memory and the computer program code are additionally configured to, working with the at least one processor, cause the apparatus at least to select whether or not to trigger an alarm based on a result of the determining.

According to one aspect of the present disclosure, there is provided an apparatus, which comprises means for measuring a skin-surface temperature at a first temperature sensor element at a measuring rate. The apparatus also comprises means for measuring an ambient temperature at a second temperature sensor element at the measuring rate. The apparatus further comprises means for calculating a plurality of first change rates for the skin-surface temperature and a plurality of second change rates for the ambient temperature over a time interval. The apparatus further comprises means for determining, based on the plurality of first change rates and the plurality of second change rates, whether an ambient temperature change rate is faster than a skin-surface temperature change rate by a threshold. The apparatus additionally comprises means for selecting whether or not to trigger an alarm based on a result of the determining.

According to another aspect of the present disclosure, there is provided an apparatus, which comprises means for receiving temperature data from a thermometer apparatus, wherein the thermometer apparatus comprises a first temperature sensor element for measuring a skin-surface temperature at a measuring rate and a second temperature sensor element for measuring an ambient temperature at the measuring rate. The apparatus also comprises means for calculating, based on the received temperature data, a plurality of first change rates for the skin-surface temperature and a plurality of second change rates for the ambient temperature over a time interval. The apparatus further comprises means for determining, based on the plurality of first change rates and the plurality of second change rates, whether an ambient temperature change rate is faster than a skin-surface temperature change rate by a threshold. The apparatus additionally comprises means for select whether or not to trigger an alarm based on a result of the determining.

According to another embodiment, a computer-readable storage medium carries one or more sequences of one or more instructions which, when executed by one or more processors, cause, at least in part, an apparatus to perform steps of the methods according to some aspects of the present disclosure.

Still other aspects, features, and advantages of the present disclosure are readily apparent from the following detailed description, simply by illustrating a number of particular embodiments and implementations. The present disclosure is also capable of other and different embodiments, and its several details can be modified in various respects, all without departing from the spirit and scope of the present disclosure. Accordingly, the drawings and description are to be regarded as illustrative in nature, and not as restrictive.

The apparatuses as discussed above in some aspects of the present disclosure are fitted with any mobile devices which are capable of providing alarms to the users, such as the parents with young children or medical staff with patients. In this manner, the movements of the children or patient, such as those engendering Tipi, may be well tracked and thereby the parents or medical staff may be timely and properly warned when such movements arise. Further, based on tracking the speed of temperature change rates of the two temperature sensor elements, it may result in fewer false alarms and improvements of the alarm accuracy. Thereby, the parents, who may sleep in their own room, would have good sleep since it is unnecessary for them to constantly worry about whether their child or children kick the quilt and frequently go to check whether the child is well covered with the quilt.

BRIEF DESCRIPTION OF THE DRAWINGS

The embodiments of the invention are illustrated by way of example, and not by way of limitation, in the figures of the accompanying drawings.

DESCRIPTION OF SOME EMBODIMENTS

Examples of methods, apparatuses, and a computer-readable storage medium for detecting body-related temperature changes are disclosed. In the following description, for the purposes of explanation, numerous specific details are set forth in order to provide a thorough understanding of various embodiments of the present disclosure. It is apparent, however, to one skilled in the art that the embodiments of the present disclosure may be practiced without these specific details or with an equivalent arrangement. In other instances, well-known structures and devices are shown in block diagram form in order to avoid unnecessarily obscuring the embodiments of the present disclosure.

Figure 1:
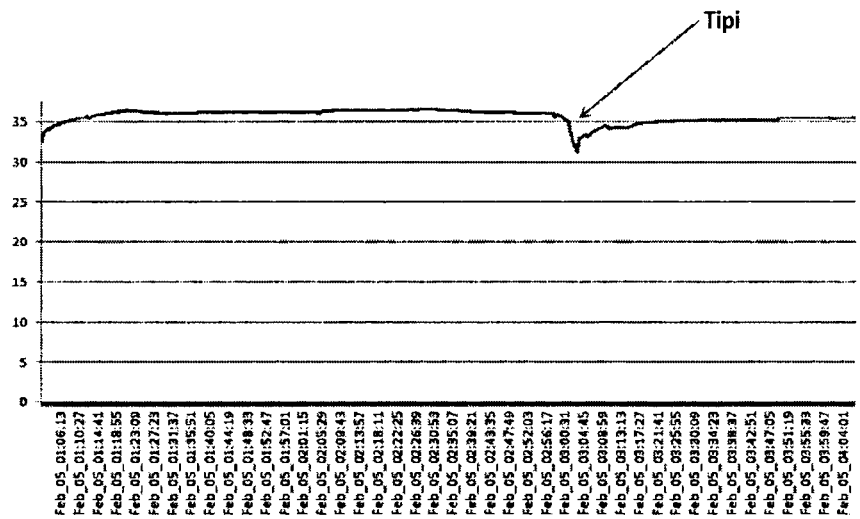
FIG. 1 is a plot schematically illustrating a monitoring curve of skin-surface temperature changes.
Figure 2:
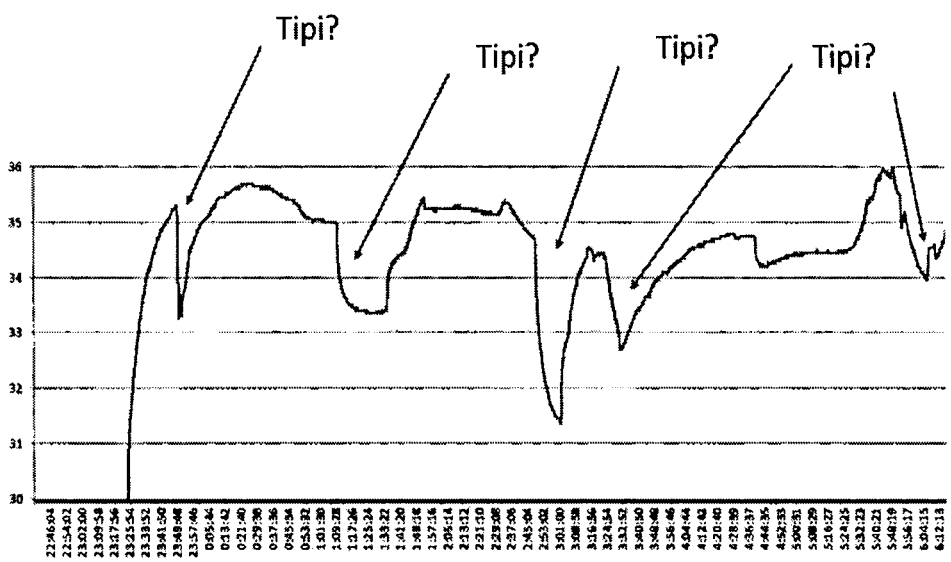
FIG. 2 is another plot schematically illustrating another monitoring curve of skin-surface temperature changes.
Figure 3:
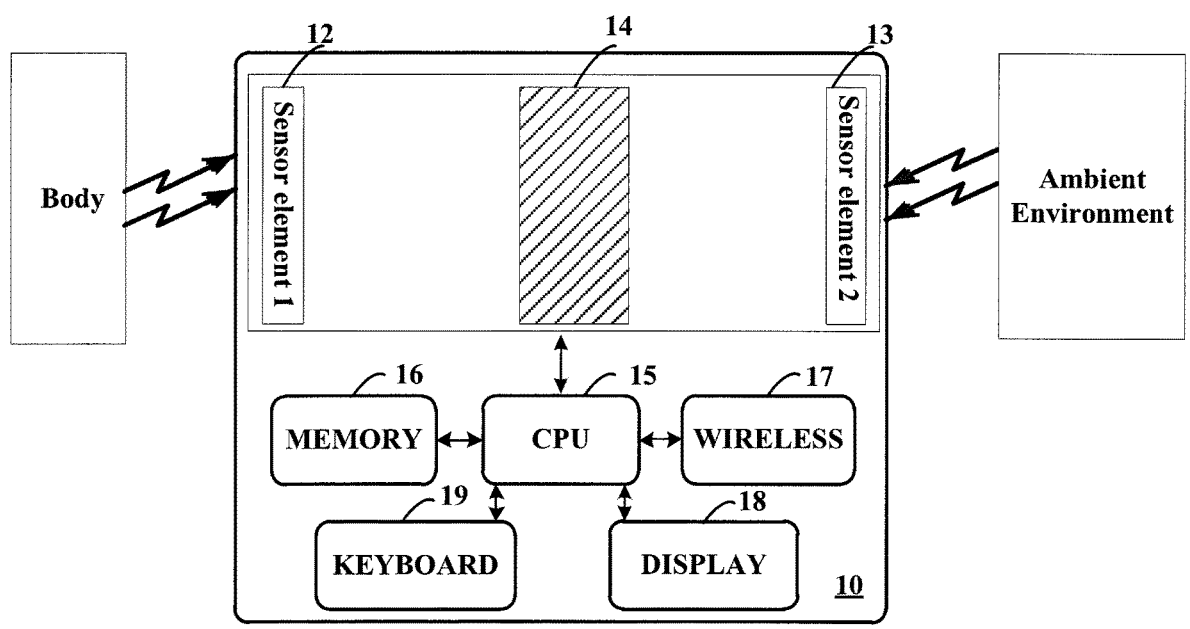
FIG. 3 is a schematic diagram illustrating a thermometer apparatus through which some example embodiments of the present disclosure may be practice.

FIG. 3 is a schematic diagram illustrating a thermometer apparatus 10 through which some example embodiments of the present disclosure may be practiced. As illustrated in FIG. 3, the thermometer apparatus 10 according to some example embodiments of the present disclosure mainly includes two portions, that is, a temperature data collecting portion and a temperature data processing portion. The temperature data collecting portion, among other thing, may include a first temperature sensor element 12, a second temperature sensor element 13, and a thermal insulating layer 14 arranged therebetween. The first temperature sensor element 12 may be used to measure a skin-surface temperature of a body, such as human-body, for example, a child's body or a patient's body, whose night activities and rest should be taken care of. The skin-surface temperature may be progressively dropping due to the kicking of quilt, for example, the occurrence of the Tipi event. The second temperature sensor element 13 may be used to measure an ambient temperature. The ambient temperature may be a temperature in the quilt or blanket when the quilt or the blanket well covers the child. The ambient temperature may turn to be a temperature of, for example, a sleeping room or a bedroom when the Tipi event takes place.

The first temperature sensor element 12 and the second temperature sensor element 13 herein may be implemented by any suitable existing thermo sensors, such as those available from the current market, for example, thermo sensors from Texas Instruments. The thermal insulating layer 14 herein may be made from any suitable thermal isolation material, such as thermal isolation cotton, as long as such thermal isolation material may efficiently reduce or eliminate hear transfer between the first temperature sensor element 12 and the second temperature sensor element 13. Accordingly, the thickness of the thermal insulating layer 14 may be determined based upon the requirements for the thermal isolation and may be further customized in view of the whole size of the thermometer apparatus 10, which, in some embodiments, is preferred to be small such that it is more easily to be portable and hand-held, and may be adapted to the skin-surface without causing irritation or discomfort to a sleeping child.

It is to be understood that the temperature data collecting portion may include one or more interfaces, which, may connect the temperature data collecting portion to the temperature data processing portion via data buses, address buses and control buses. In this manner, the temperature data sampled by the first temperature sensor elements 12 and 13 at a certain measuring or sampling rate may be transmitted to the temperature data processing portion for further processing. The transmission herein may be carried out on a regular basis according to the configuration and could be suspended or stopped by user input or at a pre-determined time.

The temperature data processing portion, among other things, may include a central processing unit ("CPU", or a processor) 15 and a memory 16 containing computer program code. The CPU 15 may be of any type suitable to the local technical environment, and may include one or more of general purpose processors, special purpose processors, microprocessors, digital signal processors ("DSPs") and processors based on multi-core processor architecture, as non-limiting examples. The computer program code is assumed to include instructions that, when executed by the CPU 15, enable the thermometer apparatus 10 to operate in accordance with some example embodiments of the present disclosure, as will be discussed later with respect to the method 20 in reference to FIGS. 4-11.

In various embodiments, the temperature data processing portion may further include a number of the peripheral interfaces, such as a wireless interface 17, a display 18 and a keyboard 19 as shown.

The wireless interface 17 may be selected from suitable wireless interfaces that are compatible to the existing or future-developed short-range wireless networking techniques, such as Bluetooth, Wi-Fi, and the like. With this wireless interface 17, the thermometer apparatus 10, in some embodiments, may communication in real time with an external device, such as a wireless terminal, for example, a cellphone, a smart phone, a laptop computer, a hand-held computer, a tablet computer, a tab, and etc.

This way, in some example embodiments of the present disclosure, upon a detection of a Tipi event through the methods as proposed by the present disclosure, the thermometer apparatus 10 may transmit an alarm message to the external device such that the user (for example, parents sleeping in a different bedroom) of the external device may be informed of an occurrence of a Tipi event. In some other example embodiments of the present disclosure, the temperature data measured by the first and second temperature sensor elements 12 and 13 may be transmitted to the external device or apparatus via the wireless interface 17 such that the methods as proposed may be merely implemented at the external device or apparatus. In other words, the external device or apparatus may determine whether a Tipi event takes place based on the received temperature data and may trigger an alarm action, such as initiating an alarm including at least one of an audible alarm, a visible alarm, and a vibrating alarm, upon determining occurrence of such Tipi event.

The display 18 is used to display to the user, or more particularly, the parents or the healthcare workers, information such as temperature graphs, temperature statistics data, the number of the alarmed Tipi events in a previous day or in the last week, and etc. The display 18 may be one of a liquid crystal display (LCD), a light emitting diode (LED) display, an organic LED (OLED) display, and a touch-sensitive display that allows input by simply touching the display screen with a finger, a stylus or a pen.

The keyboard 19 may be a simple numeric keyboard, a standard QWERTY keyboard or a virtual keyboard, which is presented on the touch-sensitive display upon a user touch. The keyboard 19 may be used to input commands or user preference items into the thermometer apparatus 10, such as for selecting an appropriate operation mode according to, for example, the age of the child to be monitored, setting a monitored time period, and a measuring or sampling rate for collecting the skin-surface temperature and the ambient temperature.

In some example embodiments, in addition to or in lieu of the keyboard 19, the thermometer apparatus 10 may additionally include a remote-control for controlling menus items presented on the display 18 and issuing commands associated with menus items presented on the display 18. The commands may include, for example, turning on or turning off the thermometer apparatus 10, setting the time period to be monitored, such as from 10:00 pm of the day to 06:30 am of the next day, and selecting operating modes, such as those provided for different children with different ages or different body mass.

It should be noted that FIG. 3 is shown for an illustrative purpose and a person skilled in the art is able to understand that the thermometer apparatus 10 may be designed in one piece with an elastic strip or a wrapping elastic band such that the thermometer apparatus 10 could be worn by the children or patients in a variety of ways. For example, the parents or the health staff may have the thermometer apparatus 10 worn at the children's wrist, elbow or ankle. In an embodiment, the thermometer apparatus 10 may be manufactured as a patch with, for example, a size and a shape similar to a button, which may be pasted on a belly or a thigh of a child, thereby delivering more convenience and comfort.

Figure 4:
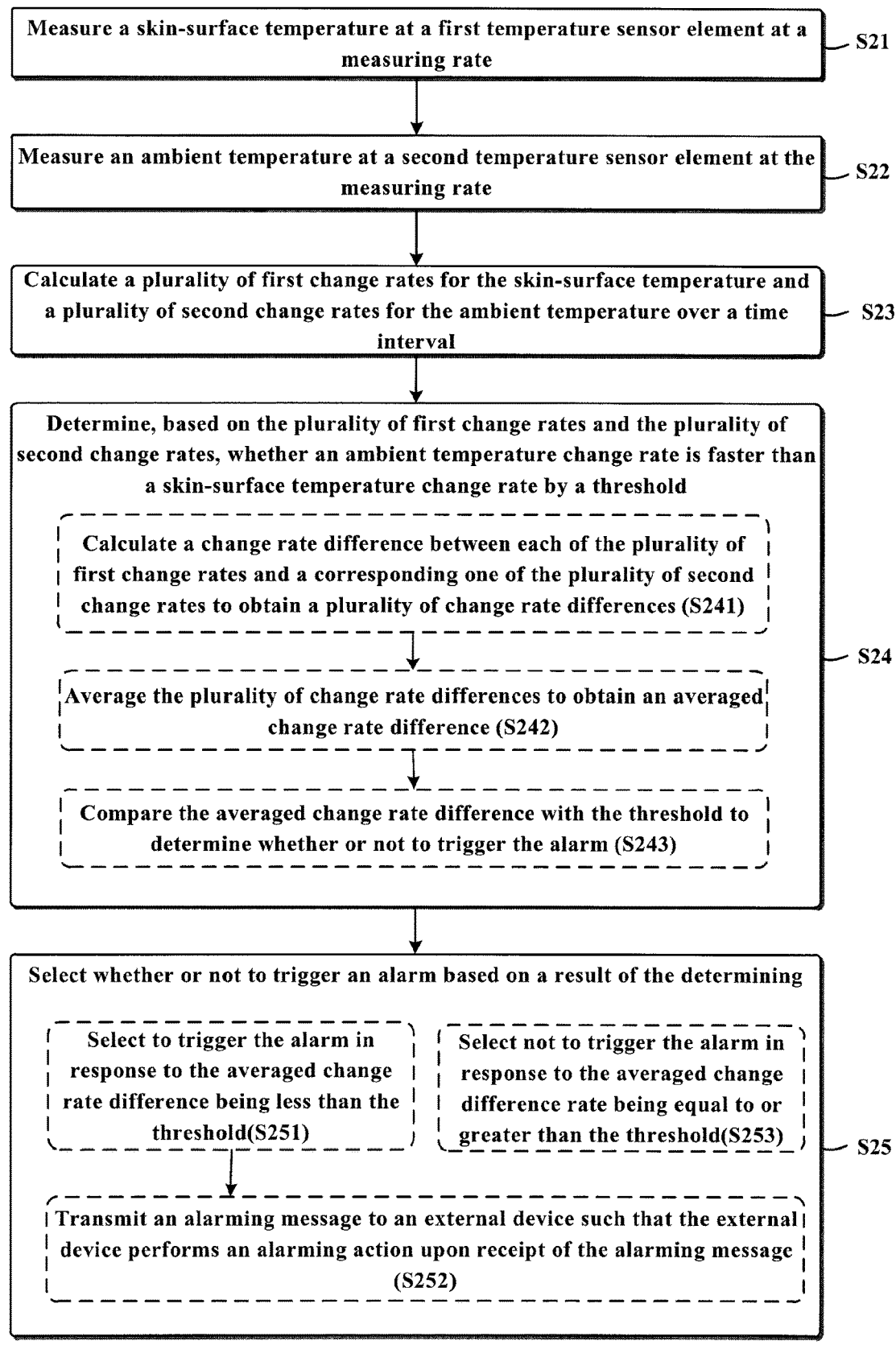
FIG. 4 is a schematic flowchart of a method for detecting body-related temperature changes according to some example embodiments of the present disclosure.

FIG. 4 is a schematic flowchart of a method 20 for detecting body-related temperature changes according to some example embodiments of the present disclosure. According to some example embodiments of the present disclosure, the method 20 may be implemented by the thermometer apparatus 10 as illustrated in FIG. 3.

As illustrated in FIG. 4, the method 20, at S21, measures a skin-surface temperature at a first temperature sensor element at a measuring rate and, at S22, measures an ambient temperature at a second temperature sensor element at the measuring rate. The first and second temperature sensor elements herein may be identical to the first and second temperature sensor elements 12 and 13 as illustrated in FIG. 3 and therefore may be implemented by any suitable existing temperature sensors. The measuring rate herein may be an appropriate sampling rate at which the first and second temperature sensor elements may measure and obtain the temperature data with respect to the skin-surface temperatures and the ambient temperatures. For example, the first and second temperature sensor elements may measure the skin-surface and the ambient temperature per two seconds.

At S23, the method 20 calculates a plurality of first change rates for the skin-surface temperature and a plurality of second change rates for the ambient temperature over a time interval. The time interval herein may be a time duration ("$T_{Duration}$") based on which one first change rate for the skin-surface temperature and one second change rate for the ambient temperature could be obtained. For example, in one embodiment, one first change rate for the skin-surface temperature may be obtained by a temperature difference between the skin-surface temperature measured at present and the skin-surface temperature measured at $T_{Duration}$ ago divided by the $T_{Duration}$. Likewise, one second change rate for the ambient temperature may equally be obtained in this manner.

At S24, the method 20 determines, based on the plurality of first change rates and the plurality of second change rates, whether an ambient temperature change rate is faster than a skin-surface temperature change rate by a threshold.

At S25 the method 20 selects whether or not to trigger an alarm based on a result of the determining.

In some example embodiments of the present disclosure, the determining at S24 may include calculating, at S241, a change rate difference between each of the plurality of first change rates and a corresponding one of the plurality of second change rates to obtain a plurality of change rate differences. At S242, the plurality of change rate differences may be averaged to obtain an averaged change rate difference. At S243, the averaged change rate difference may be compared with the threshold to determine whether or not to trigger the alarm.

In some example embodiments of the present disclosure, the selecting whether or not to trigger the alarm at S25 may comprise selecting to trigger the alarm in response to the averaged change rate difference being less than the threshold at S251. Thereby, at S252, an alarm message may be transmitted to an external device such that the external device performs an alarm action upon receipt of the alarm message.

As mentioned before, the external device herein may be a mobile station, such as a smart phone, which may have been kept near the parents, for example, on a bedside table. When the alarm message is received from the thermometer apparatus 10, the smart phone may be triggered to raise one of an audible alarm, a visible alarm, and a vibrating alarm to the parents according to the user's preference and configuration. After that, the parents may be waked up by the alarm and immediately know that their child is sleeping naked, for example, the quilt being kicked. Then, the parents may go to the child's bedroom and cover the quilt for him or her quickly.

In some example embodiments of the present disclosure, the selecting whether or not to trigger the alarm at S25 may comprise selecting not to trigger the alarm in response to the averaged change difference rate being equal to or greater than the threshold at S253.

From the above descriptions with reference to FIG. 4, it is to be understood that alarm accuracy for informing the parents or healthcare workers of the occurrence of the Tipi or Tipi-like events could be notably improved based on whether the ambient temperature change rate (or dropping speed) is faster than the skin-surface temperature change rate (or dropping speed). Further, based on a proper threshold, which may be determined according to experimental statistics, the number of the false alarms.

For a better understanding of the example embodiments of the present disclosure, the following will elaborate details of how to determine and trigger an alarm message to the external device via pseudo codes together with reference to FIGS. 5-11.

Below are example pseudo codes according to some example embodiments of the present disclosure:

Set T_sensor1=TA T_sensor2=TB

/*TA denotes a skin-surface temperature as measured by the first temperature sensor element 12 as shown in FIG. 3, and TB denotes an ambient temperatures as measured by the second temperature sensor element 13 as shown in FIG. 3. Assume T_body denotes skin temperature. After the child sleeps for a while with the thermometer apparatus 10 attached to the child and inside the quilt, based on the heat exchange principle, TA=T_body, and after a period of time, TB=TA, that is, TB=TA=T_body. If the quilt is kicked, the skin-surface temperature and the ambient temperature (temperature inside the quilt and outside the quilt when the kicking arise) changes but the temperature changing rate is different.*/

Figure 5:
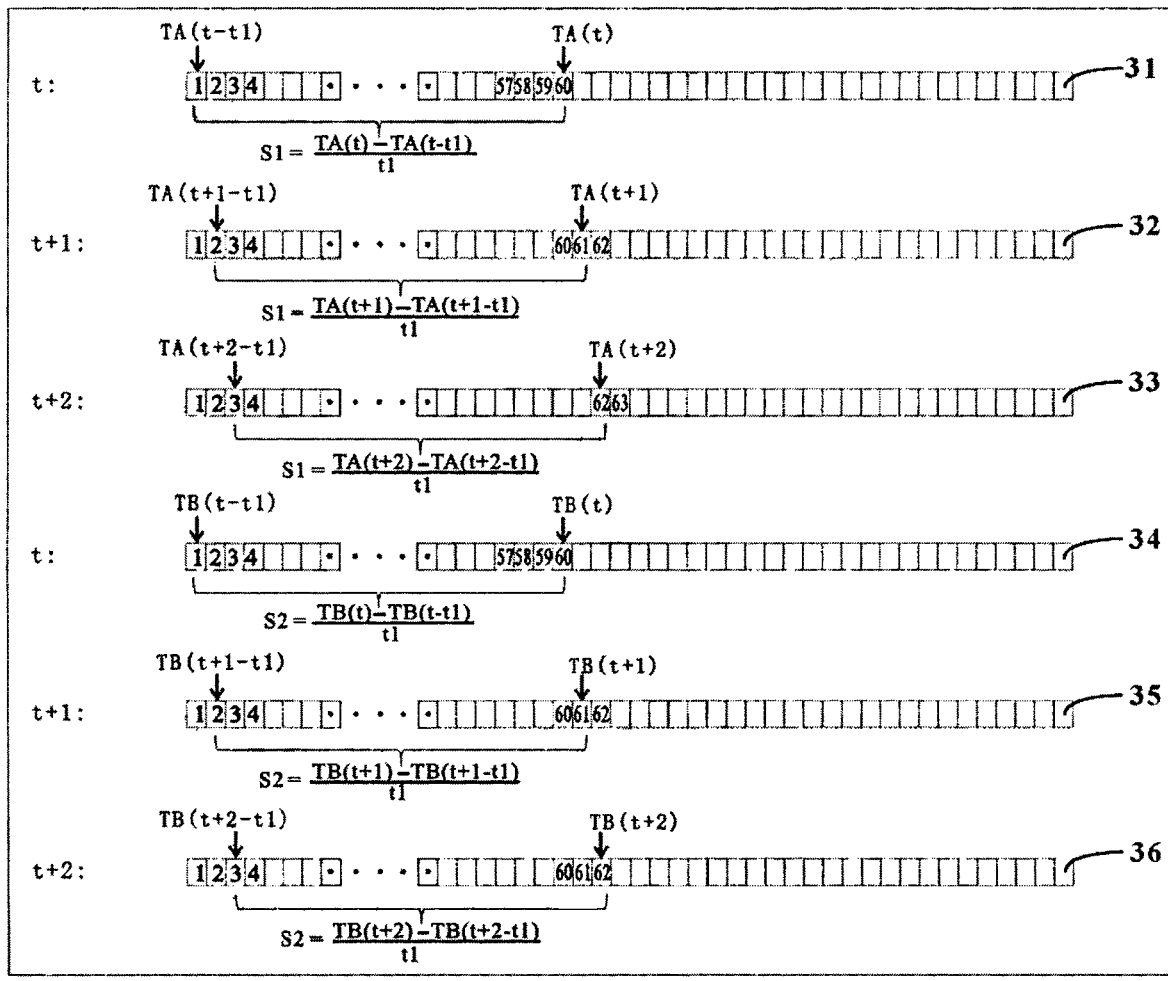
FIG. 5 is a schematic diagram illustrating a process for obtaining change rates of the skin-surface temperatures and the ambient temperatures, respectively, according to some example embodiments of the present disclosure.

Set t1=60/*a unit interval which lasts about 2 minutes (for example, 120 seconds) in time duration, assuming that the first temperature sensor element 12 measures or samples the skin-surface temperature every 2 seconds. This unit interval is shown in FIG. 5, which spans from the TA (t−t1) to the TA (t) or from the TB(t−t1) to the TB (t), wherein the "t" denotes a location of the present time (indicated by "60" at 31) and "t−t1" denotes a location of a time that is t1 ago (indicated by "1" at 31), both depicted in a form of a small box, each lasting 2 seconds*/

Set $$S1 = \frac{TA(t) - TA(t-t1)}{t1} /*$$

which is a changing rate of TA in the unit interval t1, as illustrated at 31 in FIG. 3, and which may be expressed in degrees/second, for example, C/sec*/

Set $$S2 = \frac{TB(t) - TB(t-t1)}{t1} /*$$

which is a changing rate of TB in the unit interval t1, as illustrated at 34 in FIG. 3, and which may also be expressed in degrees/second*/

Set S3=S2−S1/*which is to calculate a change rate difference between S1 and S2 and the first S3 is obtained at the box 60 where the first S1 and the first S2 have been calculated and thus a mutual difference (for example, the first S3) could be obtained*/

Set t2=20/*a unit interval which lasts about 40 seconds. After the duration of the t2, twenty S3s would be obtained, as indicated in FIG. 6 at 41, 42, and 43*/

Figure 6:
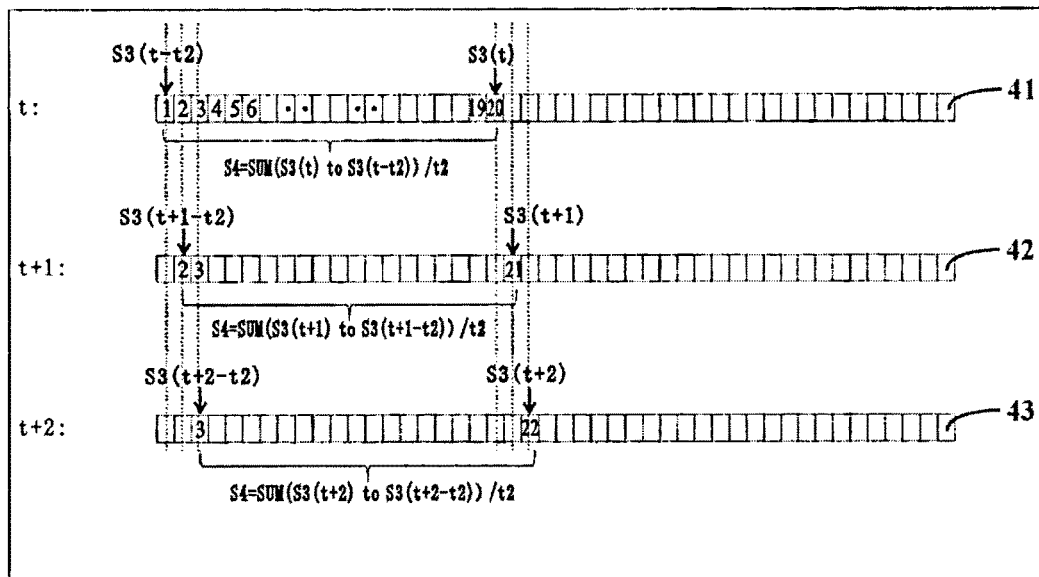
FIG. 6 is a schematic diagram illustrating a process for obtaining an averaged change rate difference according to some example embodiments of the present disclosure.

Set $$S4 = \frac{S3(t) + S3(t-1) + S3(t-2) + \ldots + S3(t-t2)}{t2} /*$$

which is to average the plurality of change rate differences S3 that are obtained in the duration of "t2" to obtain an averaged change rate difference, as indicated in FIG. 6, at 41, 42 and 43, and which may be expressed in degrees/second$^2$, for example, C/sec$^2$*/

```
If (S1<0) and (S2<0)
    Then Return S4 /*that is, if the temperature change of one of the
skin-surface temperature and the ambient temperature is rising rather
then dropping, then loop the flow from the beginning */
    ELSE Return 0 /*meaning that the flow will proceed*/
    Set Smin=−0.015 /*a threshold which could be set based upon
    empirical values */
    IF S4<Smin
    THEN Return RESULT="Tipi"/*which is to trigger an alarm
since the averaged change rate difference S4 is less than the threshold */
```

It should be noted that the above example pseudo codes are only illustrative of the method according to the present disclosure and the method should not be limited to this specific form. A person skilled in the art may amend, revise or modify some of these pseudo codes based upon the teaching of the present disclosure in connection with various example embodiments such that the method could achieve high operation efficiency or accomplish other additional tasks.

The below will further illustrate the processing operations as shown in the above pseudo codes using experimental temperature data, with reference to FIGS. 7-11.

Figure 7:
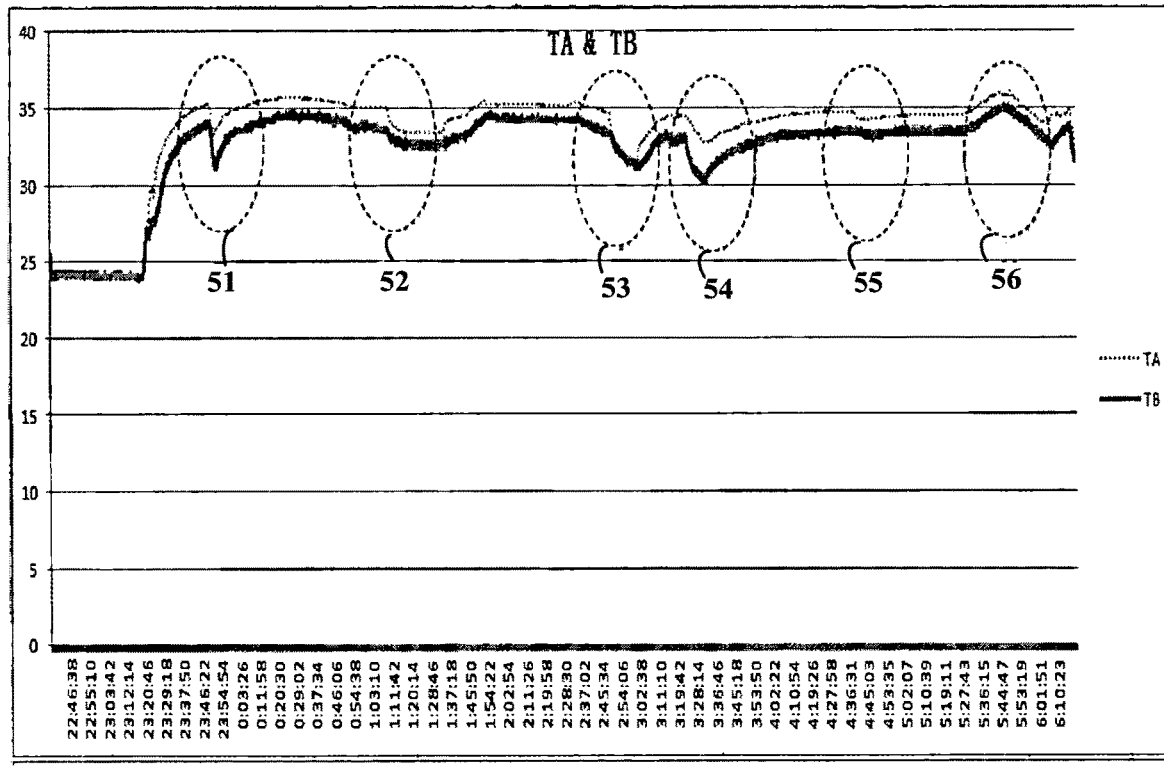
FIG. 7 is a schematic plot illustrating experimental temperature data obtained during a period of time from the skin-surface temperature sensor element and the ambient temperature sensor element, respectively, according to some example embodiments of the present disclosure.

FIG. 7 is a schematic plot illustrating experimental temperature data obtained during a period of time from the skin-surface temperature sensor element and the ambient temperature sensor element, respectively, according to some example embodiments of the present disclosure.

As illustrated in FIG. 7, a changing trend of TA and changing trend of TB are respectively shown according to the real temperature changing data obtained from experiments. The real Tipi event happened at observation points 51 and 54, that are, around at 23:51 pm and 3:29 am.

Figure 8A:
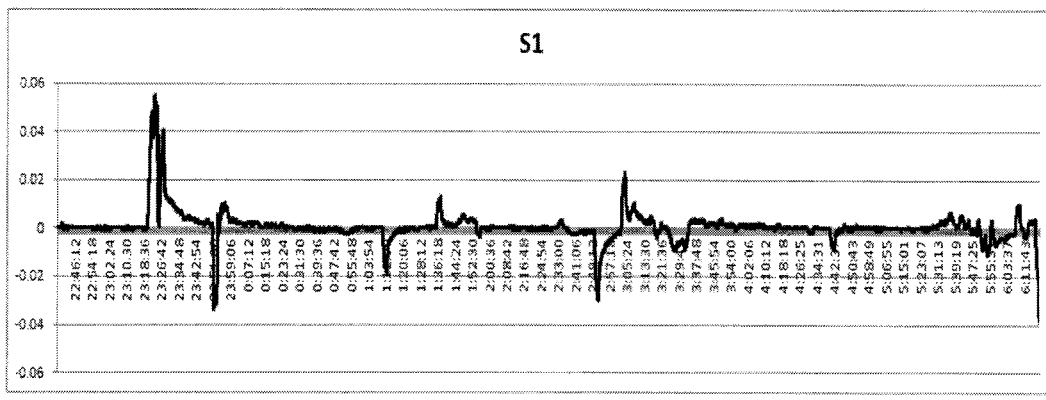
FIGS. 8a-8b are schematic plots illustrating change rates of the skin-surface temperatures and the ambient temperatures, respectively, according to some example embodiments of the present disclosure.
Figure 8B:
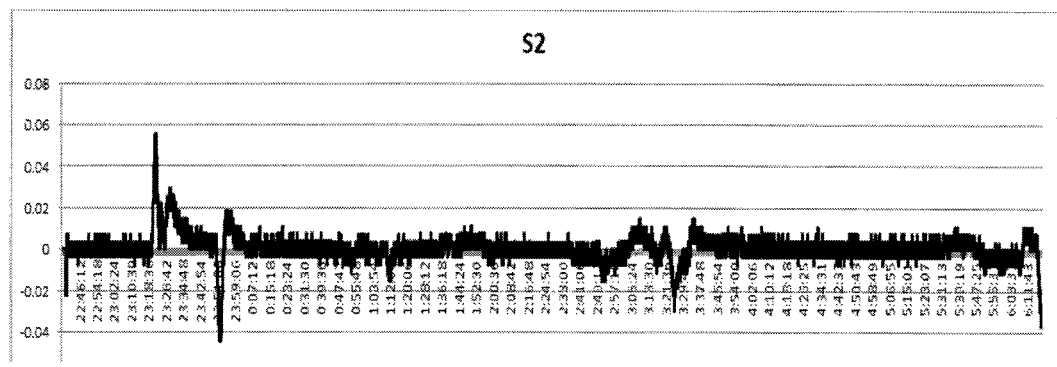
Figure 9:
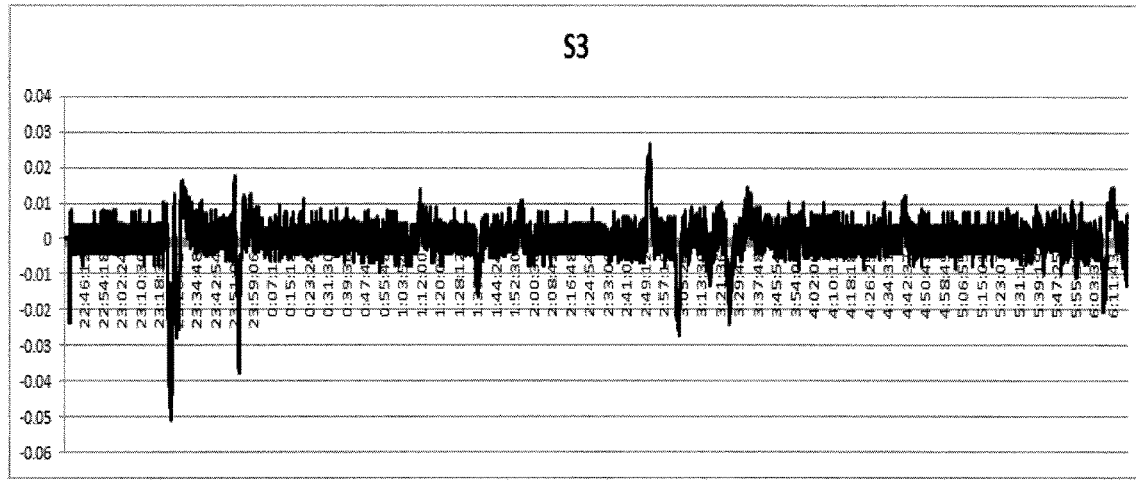
FIG. 9 is a schematic plot illustrating change rate differences between the skin-surface temperatures and the ambient temperatures according to some example embodiments of the present disclosure.
Figure 10:
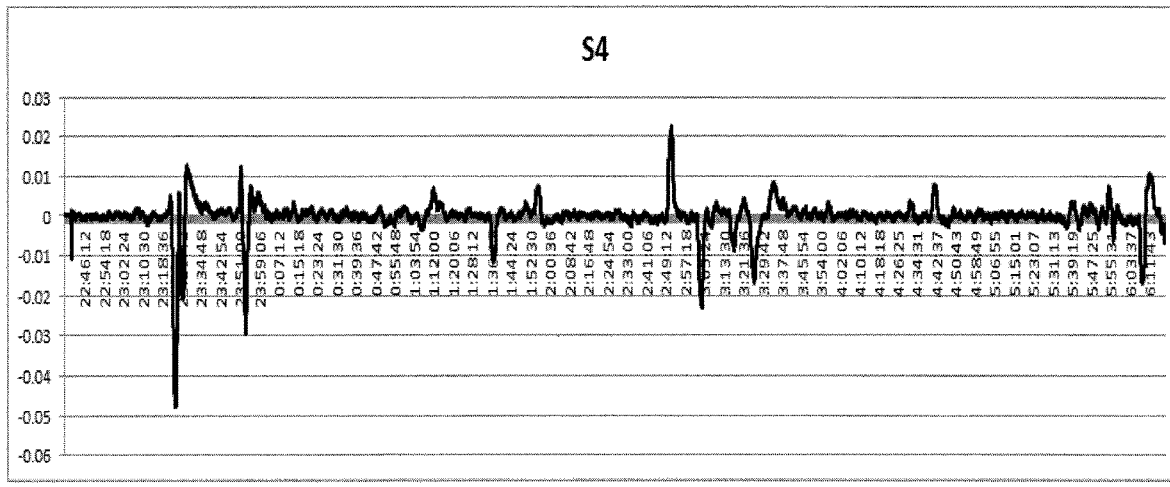
FIG. 10 is a schematic plot illustrating averaged change rate differences according to some example embodiments of the present disclosure.

FIG. 8a and FIG. 8b are schematic plots illustrating change rates of the skin-surface temperatures and the ambient temperatures (S1 and S2), respectively, obtained based on the same experimental temperature data. FIG. 9 shows a schematic plot illustrating change rate differences (S3) between the skin-surface temperatures and the ambient temperatures based on the S1 and S2 that are respectively illustrated in FIGS. 8a and 8b. As can be seen from FIG. 9, although the values of S3 are obtained, it is still not easy to identify the occurrence of Tipi event due to noise. To this end, according to the above pseudo codes, this noise may be filtered out by averaging the plurality of change rate differences S3, that is, calculating the averaged change rate differences S4, which is illustrated in FIG. 10.

Further noise could be filtered out based on the below pseudo codes:

```
IF (S1 < 0) AND (S2 < 0) THEN Return S4
    ELSE Return 0
```

Figure 11:
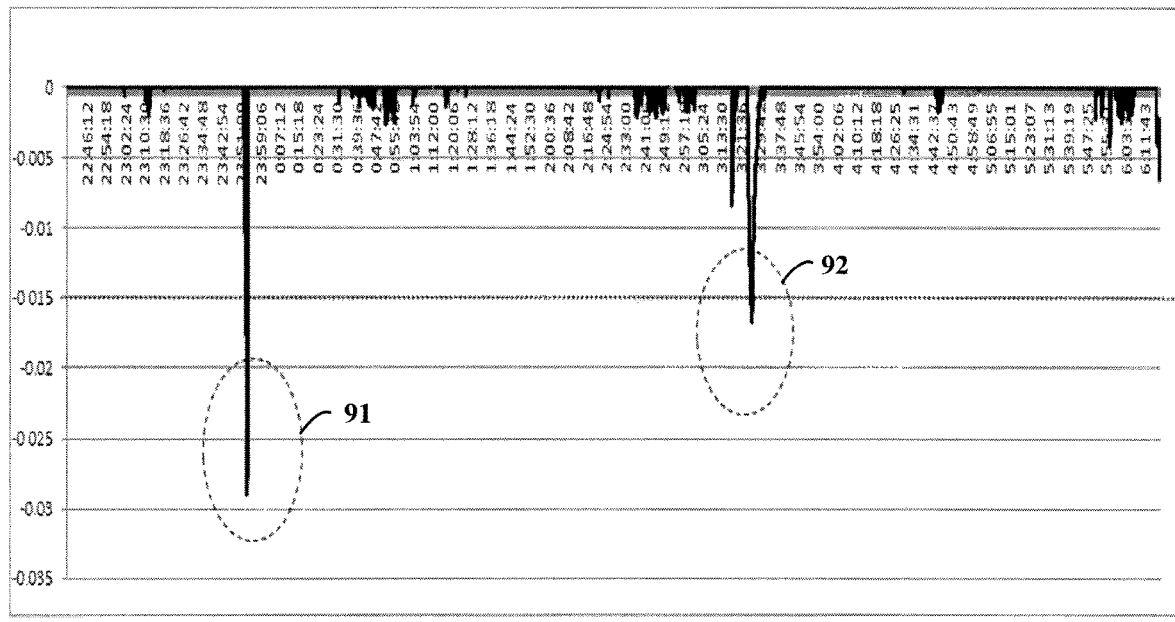
FIG. 11 is a schematic plot illustrating final results that may trigger alarms according to some example embodiments of the present disclosure.

As shown in FIGS. 8a and 8b, both S1 and S2 are lower than 0 at several points such as 23:51 pm and 3:29 am, then these points could be excluded and further results are obtained as shown in FIG. 11.

FIG. 11 is a schematic plot illustrating final results that may trigger alarms according to some example embodiments of the present disclosure.

As mentioned before, a threshold Smin=−0.015 is set and based on this threshold, it can be seen from FIG. 11 that the values of S4 at the points around 23:51 pm ("91" as shown) and 3:29 am ("92" as shown) are less than the threshold Smin. As a result, it can be determined that Tipi event may occur at these two points 91 and 92.

The above discusses in detail about the algorithm as proposed by the present disclosure to determine the actual Tipi event. However, these discussions are only for illustrative purposes and a person skilled in the art may add or modify some steps or operations to achieve additional effect without deviating from the spirit and scope of the present disclosure. For example, although the threshold Smin=−0.015 is applied herein, the value of the threshold may not be limited to this specific one but could be properly selected from a range, such as −0.010~−0.030 or −0.007~−0.017 as shown in FIG. 11, such that different alarm requirements or modes may be achieved.

Figure 12:
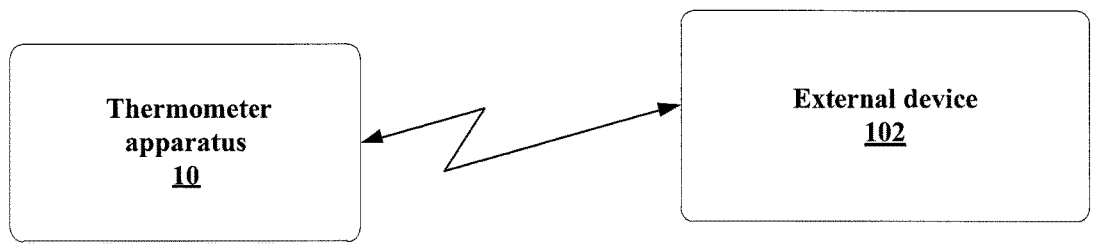
FIG. 12 is a schematic diagram illustrating an interaction between the thermometer apparatus as illustrated in FIG. 3 and an external device according to some example embodiments of the present disclosure.

FIG. 12 is a schematic diagram illustrating an interaction between the thermometer apparatus 10 as illustrated in FIG. 3 and an external device 102 according to some example embodiments of the present disclosure. As previously discussed with reference to FIG. 3, the interaction between the thermometer apparatus 10 and the external device 102 could be implemented by one or more wireless interfaces (or modules) built in the thermometer apparatus 10. The wireless interface herein may be compatible with short-range wireless communication standards, for example Bluetooth, Wi-Fi (802.11), near field communication ("NFC"), ZigBee, Wimedia, IrDA, to name a few.

In some example embodiments of the present disclosure, the thermometer apparatus 10 may measure and collect the temperature data regarding the skin-surface temperature and the ambient temperature and further determine whether or not to trigger an alarm, as discussed previously with reference to FIG. 4.

In some example embodiments of the present disclosure, the temperature data with respect to the skin-surface temperature and the ambient temperature may be transferred wirelessly to the external device through the wireless interface. By means of the collection of the temperature data from the thermometer apparatus 10, the external device 102 may by itself determine to raise an alarm if the ambient temperature change rate is faster than the skin-surface temperature change rate by the threshold. In other words, the external device 102 may play a role of a decision-maker to issue an alarm instead of the thermometer apparatus 10. In this manner, the thermometer apparatus 10 is only responsible for collecting the skin-surface temperature and the ambient temperature and transferring the collected temperature data to the external device and thereby the processing and storage cost of the thermometer apparatus 10 could be notably lowered since most of the operations would be carried out at the external device 102.

Figure 13:
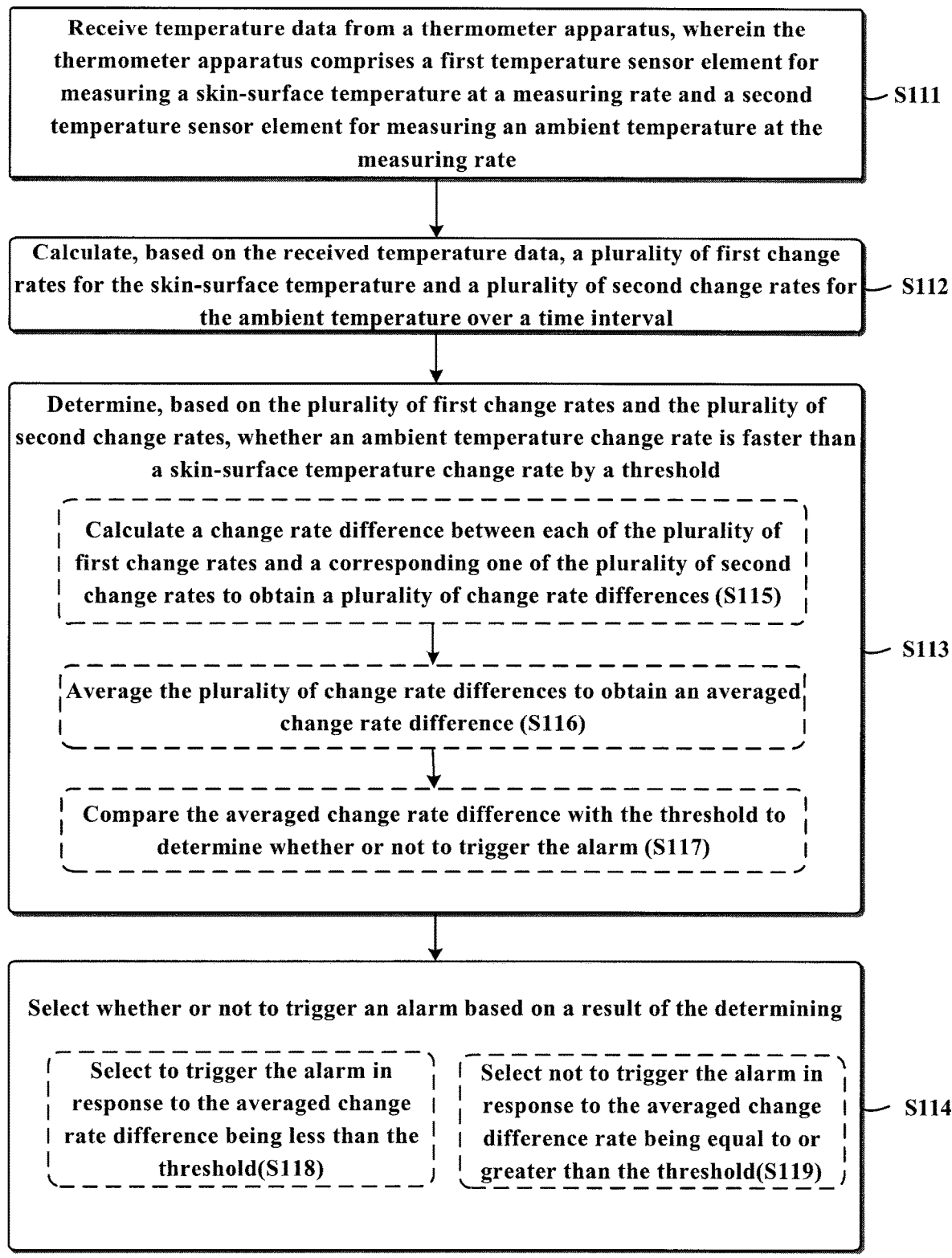
FIG. 13 is a flowchart of another method for detecting body-related temperature changes according to some example embodiments of the present disclosure.

For a better understanding of the above example embodiments, the following will describe the operations implemented by the external device for determining whether an alarm is necessary with reference to FIG. 13.

FIG. 13 is a flowchart of another method 110 for detecting body-related temperature changes according to some example embodiments of the present disclosure. It is to be understood that the method 110 may be performed by the external device or apparatus.

As illustrated in FIG. 13, the method 110 receives, at S111, temperature data from a thermometer apparatus, wherein the thermometer apparatus comprises a first temperature sensor element for measuring a skin-surface temperature at a measuring rate and a second temperature sensor element for measuring an ambient temperature at the measuring rate. The thermometer apparatus herein may be identical to the one shown and discussed with reference to FIG. 3.

Then, at S112, the method 110 calculates, based on the received temperature data, a plurality of first change rates for the skin-surface temperature and a plurality of second change rates for the ambient temperature over a time interval.

After calculating the plurality of first and second change rates, the method 110 proceeds to S113, at which the method 110 determines, based on the plurality of first change rates and the plurality of second change rates, whether an ambient temperature change rate is faster than a skin-surface temperature change rate by a threshold. Then, at S114, the method 110 selects whether or not to trigger an alarm based on a result of the determining.

In some embodiments of the present disclosure, the determining as performed at S113 may comprise calculating a change rate difference between each of the plurality of first change rates and a corresponding one of the plurality of second change rates to obtain a plurality of change rate differences at S115. Then, at S116, the plurality of change rate differences may be averaged to obtain an averaged change rate difference. After that, at S117, the averaged change rate difference may be compared with the threshold to determine whether or not to trigger the alarm.

In some example embodiments of the present disclosure, the selecting whether or not to trigger the alarm at S114 may comprise selecting to trigger the alarm in response to the averaged change rate difference being less than the threshold at S118 and selecting not to trigger the alarm in response to the averaged change difference rate being equal to or greater than the threshold at S119.

In some example embodiments of the present disclosure, the alarm may include at least one of an audible alarm, a visible alarm, and a vibrating alarm.

From the above discussions made in reference to FIG. 13, it is to be understood that the determining algorithm as proposed by the present disclosure may also be implemented at the external device, such as a smart phone. Since the determining algorithm regarding whether or not to trigger the alarm run at the thermometer apparatus and the one run at the external device are the same, the details about this determining algorithm as discussed with reference to FIGS. 3 and 4 may be equally applied to the external device and therefore further details are omitted herein for a simplifying purpose. Further, in some example embodiments, whether the thermometer apparatus or the external device to perform the determining algorithm may be configured or selected by the user.

Figure 14:
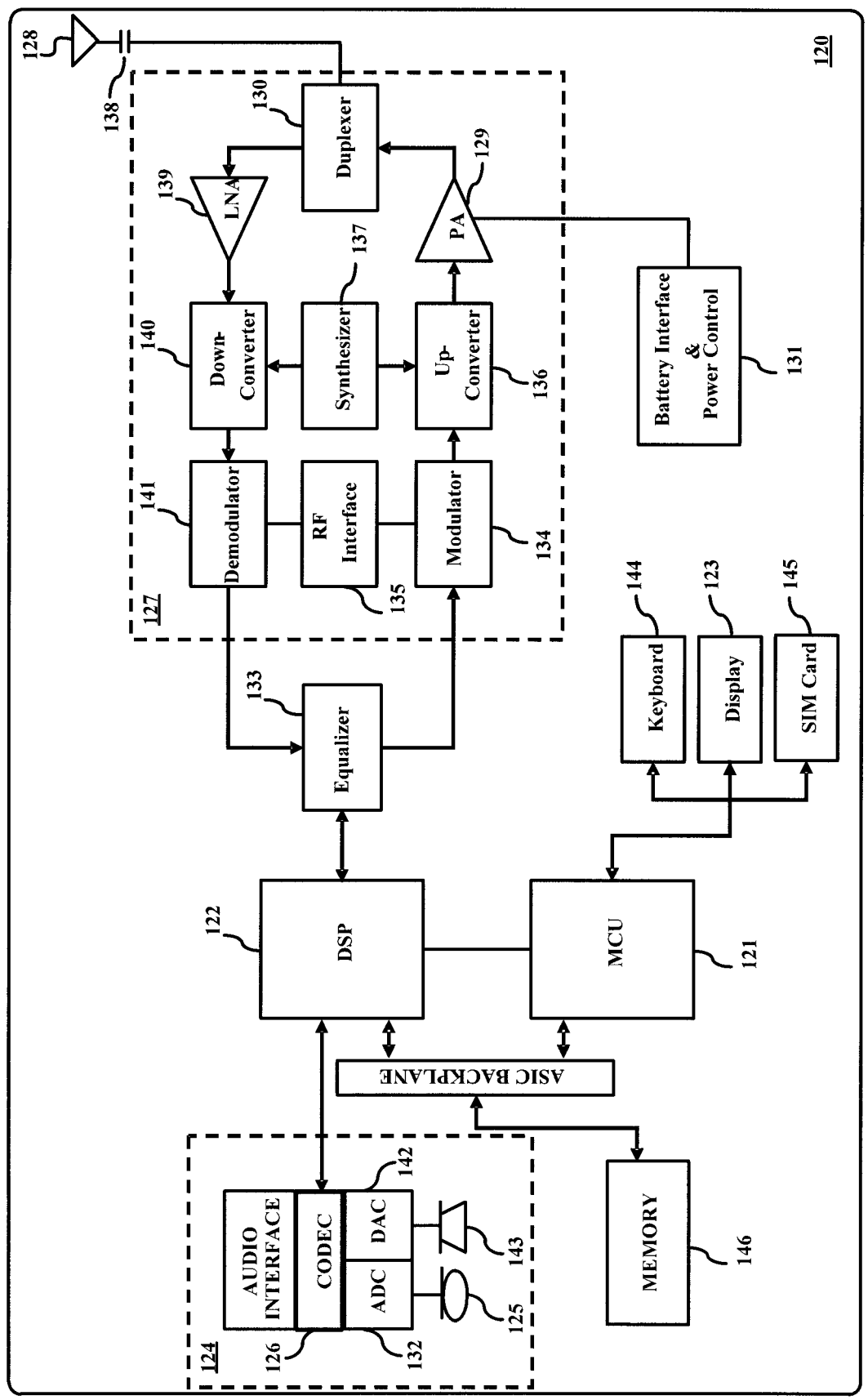
FIG. 14 is a schematic block diagram of an apparatus (for example, mobile terminal) that may be used to implement some example embodiments of the present disclosure.

FIG. 14 is a schematic block diagram of an apparatus 120 (for example, mobile terminal) that may be used to implement some example embodiments of the present disclosure. In some embodiments, the apparatus 120, or a portion thereof, constitutes a means for performing one or more steps as discussed with reference to FIG. 11. Generally, a radio receiver is often defined in terms of front-end and back-end characteristics. The front-end of the receiver encompasses all of the Radio Frequency ("RF") circuitry whereas the back-end encompasses all of the base-band processing circuitry.

Pertinent internal components of the apparatus 120 include a Main Control Unit ("MCU") 121, a Digital Signal Processor ("DSP") 122, and a receiver/transmitter unit including a microphone gain control unit and a speaker gain control unit. A main display unit 123 provides a display to the user in support of various applications and functions that perform or support the steps as discussed with reference to FIG. 11. The display 123 includes display circuitry configured to display at least a portion of a user interface of the apparatus 120. Additionally, the display 123 and display circuitry are configured to facilitate user control of at least some functions of the apparatus 120. An audio function circuitry 124 includes a microphone 125 and microphone amplifier that amplifies the speech signal output from the microphone 125. The amplified speech signal output from the microphone 125 is fed to a coder/decoder (CODEC) 126.

A radio section 127 amplifies power and converts frequency in order to communicate with a base station, which is included in a mobile communication system, via antenna 128. The power amplifier (PA) 129 and the transmitter/modulation circuitry are operationally responsive to the MCU 121, with an output from the PA 129 coupled to the duplexer 130 or circulator or antenna switch, as known in the prior art. The PA 129 also couples to a battery interface and power control unit 131.

In use, a user of the apparatus 120 speaks into the microphone 125 and his or her voice along with any detected background noise is converted into an analog voltage. The analog voltage is then converted into a digital signal through the Analog to Digital Converter (ADC) 132. The control unit 121 routes the digital signal into the DSP 122 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, for example, microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 133 for compensation of any frequency-dependent impairments that occur during transmission though the air such as phase and amplitude distortion. After equalizing the bit stream, the modulator 134 combines the signal with a RF signal generated in the RF interface 135. The modulator 134 generates a sine wave by way of frequency or phase modulation. In order to prepare the signal for transmission, an up-converter 136 combines the sine wave output from the modulator 134 with another sine wave generated by a synthesizer 137 to achieve the desired frequency of transmission. The signal is then sent through a PA 129 to increase the signal to an appropriate power level. In practical systems, the PA 129 acts as a variable gain amplifier whose gain is controlled by the DSP 122 from information received from a network base station. The signal is then filtered within the duplexer 130 and optionally sent to an antenna coupler 138 to match impedances to provide maximum power transfer. Finally, the signal is transmitted via antenna 128 to a local base station. An automatic gain control ("AGC") can be supplied to control the gain of the final stages of the receiver. The signals may be forwarded from there to a remote telephone which may be another cellular telephone, the thermometer apparatus 10 as illustrated in FIG. 3, any other mobile phone or a land-line connected to a Public Switched Telephone Network ("PSTN"), or other telephony networks.

Voice signals transmitted to the apparatus 120 are received via antenna 128 and immediately amplified by a low noise amplifier ("LNA") 139. A down-converter 140 lowers the carrier frequency while the demodulator 141 strips away the RF leaving only a digital bit stream. The signal then goes through the equalizer 133 and is processed by the DSP 122. A Digital to Analog Converter ("DAC") 142 converts voice signal and the resulting output is transmitted to the user through the speaker 143, all under control of a Main Control Unit (MCU) 121 which can be implemented as a Central Processing Unit ("CPU").

The MCU 121 receives various signals including input signals from the keyboard 144. The keyboard 144 and/or the MCU 121 in combination with other user input components (for example, the microphone 125) comprise a user interface circuitry for managing user input. The MCU 121 runs a user interface software to facilitate user control of at least some functions of the apparatus 120 to, for example, receive the temperature data and determine whether or not to trigger the alarm if a Tipi event is detected. The MCU 121 also delivers a display command and a switch command to the display 123 and to the speech output switching controller, respectively. Further, the MCU 121 exchanges information with the DSP 122 and can access an optionally incorporated SIM card 145 and a memory 146. In addition, the MCU 121 executes various control functions required of the apparatus 120.

The memory device 146 stores various data including call incoming tone data and is capable of storing other data including temperature data received from the thermometer apparatus and computer program codes or instructions for performing each operation as shown in FIG. 13. The software module could reside in RAM memory, flash memory, registers, or any other form of writable storage medium known in the art. The memory device 146 may be, but not limited to, a single memory, ROM, RAM, EEPROM, optical storage, magnetic disk storage, flash memory storage, or any other non-volatile storage medium capable of storing digital data, such as the temperature data.

While the disclosure has been described in connection with a number of embodiments and implementations, the disclosure is not so limited but covers various obvious modifications and equivalent arrangements, which fall within the purview of the appended claims. Although features of the disclosure are expressed in certain combinations among the claims, it is contemplated that these features can be arranged in any combination and order.

What is claimed is:

1. A method, comprising:
measuring, by an apparatus, a skin-surface temperature at a first temperature sensor element of the apparatus, at a measuring rate;
measuring, by the apparatus, an ambient temperature at a second temperature sensor element of the apparatus at the measuring rate;
calculating, by the apparatus, to obtain a plurality of change rate differences between each of a plurality of first change rates for the skin-surface temperature and a corresponding one of a plurality of second change rates for the ambient temperature over a time interval;
averaging the plurality of change rate differences between each of the plurality of first change rates and the corresponding one of the plurality of second change rates to obtain an averaged change rate difference;
determining, by the apparatus, based on the averaged change rate difference, that the change rate of the ambient temperature over the time interval is different than the change rate of the skin-surface temperature and that at least one change rate difference of the plurality of change rate differences between each of the plurality of first change rates and the corresponding one of the plurality of second change rates is less than a threshold associated with the time interval; and based on the determining, transmitting to an external device, by the apparatus, an alarm message by the apparatus to trigger an alarm action at the external device upon receipt of the alarm message at the external device.

2. The method according to claim 1, wherein a thermal insulating layer is arranged between the first temperature sensor element and the second temperature sensor element.

3. The method according to claim 1, wherein the determining comprises:

comparing the averaged change rate difference with the threshold to determine to transmit the alarm message to trigger the alarm action at the external device.

4. The method according to claim 1, wherein the alarm action comprises at least one of an audible alarm, a visible alarm, and a vibrating alarm.

5. An apparatus, comprising:

at least one processor, and at least one memory including computer program code, wherein the at least one memory and the computer program code are configured, with the at least one processor, to cause the apparatus at least to:

measure a skin-surface temperature at a first temperature sensor element at a measuring rate;

measure an ambient temperature at a second temperature sensor element at the measuring rate;

calculate to obtain a plurality of change rate differences between each of a plurality of first change rates for the skin-surface temperature and a corresponding one of a plurality of second change rates for the ambient temperature over a time interval;

average the plurality of change rate differences between each of the plurality of first change rates and the corresponding one of the plurality of second change rates to obtain an averaged change rate difference;

determine, based on the averaged change rate difference, that the change rate of the ambient temperature over the time interval is different than the change rate of the skin-surface temperature, and that at least one change rate difference of the plurality of change rate differences between each of the plurality of first change rates and the corresponding one of the plurality of second change rates is less than a threshold associated with the time interval; and based on the determining, transmit to an external device an alarm message by the apparatus to trigger an alarm action at the external device, upon receipt of the alarm message at the external device.

6. The apparatus according to claim 5, wherein a thermal insulating layer is arranged between the first temperature sensor element and the second temperature sensor element.

7. The apparatus according to claim 5, wherein the at least one memory and the computer program code are further configured to, working with the at least one processor, cause the apparatus at least to:

compare the averaged change rate difference with the threshold to determine to transmit the alarm message to trigger the alarm action at the external device.

8. The apparatus according to claim 5, wherein the alarm action comprises at least one of an audible alarm, a visible alarm, and a vibrating alarm.

9. A method, comprising:

receiving, by a device, an alarm message comprising temperature data from a thermometer apparatus, wherein the thermometer apparatus comprises a first temperature sensor element for measuring a skin-surface temperature at a measuring rate and a second temperature sensor element for measuring an ambient temperature at the measuring rate; and triggering an alarm action at the device based on the receiving the alarm message, wherein the alarm message is generated based on at least:

calculating, by the thermometer apparatus, based on the temperature data, to obtain a plurality of change rate differences between each of a plurality of first change rates for the skin-surface temperature and a corresponding one of a plurality of second change rates for the ambient temperature over a time interval;

averaging, by the thermometer apparatus, the plurality of change rate differences between each of the plurality of first change rates and the corresponding one of the plurality of second change rates to obtain an averaged change rate difference; and determining, by the thermometer apparatus, based on the averaged change rate difference, that the change rate of the ambient temperature over the time interval is different than the change rate of the skin-surface temperature and that at least one change rate difference of the plurality of change rate differences between each of the plurality of first change rates and the corresponding one of the plurality of second change rates is less than a threshold associated with the time interval.

10. The method according to claim 9, wherein the determining, by the thermometer apparatus, comprises:

comparing the averaged change rate difference with the threshold to determine to transmit the alarm message to trigger the alarm action.

* * * * *